United States Patent [19]

Taylor

[11] Patent Number: 4,500,628

[45] Date of Patent: Feb. 19, 1985

[54] PROCESS OF MAKING SOLID STATE DEVICES USING SILICON CONTAINING ORGANOMETALLIC PLASMA DEVELOPED RESISTS

[75] Inventor: Gary N. Taylor, Bridgewater, N.J.

[73] Assignee: AT&T Bell Laboratories, Murray Hill, N.J.

[21] Appl. No.: 507,929

[22] Filed: Jun. 27, 1983

Related U.S. Application Data

[62] Division of Ser. No. 256,604, Apr. 22, 1981, Pat. No. 4,396,704.

[51] Int. Cl.³ .......................... G03C 5/00; G03C 5/24; H05K 3/00
[52] U.S. Cl. ...................................... 430/311; 430/17; 430/18; 430/321; 430/325; 430/271; 430/281; 430/272; 430/966; 430/967; 427/43.1; 427/53.1; 156/643; 156/659.1
[58] Field of Search .............. 430/311, 325, 321, 271, 430/281, 17, 18, 272, 966, 967; 427/43.1, 53.1; 156/643, 659.1

[56] References Cited

U.S. PATENT DOCUMENTS

| | | | |
|---|---|---|---|
| 3,782,940 | 1/1974 | Ohto et al. | 430/287 |
| 3,809,686 | 5/1974 | Chandross et al. | 430/494 |
| 3,899,338 | 8/1975 | Lewis | 430/282 |
| 4,061,829 | 12/1977 | Taylor | 430/967 |
| 4,232,110 | 11/1980 | Taylor | 430/311 |
| 4,235,958 | 11/1980 | Barrand et al. | 430/271 |
| 4,278,753 | 7/1981 | Lewis et al. | 430/325 |
| 4,307,178 | 12/1981 | Kaplan et al. | 430/296 |
| 4,329,418 | 5/1982 | Khy et al. | 427/43.1 |
| 4,332,879 | 6/1982 | Pastor | 430/311 |
| 4,347,304 | 8/1982 | Sakurai et al. | 430/325 |
| 4,396,704 | 8/1983 | Taylor | 430/321 |

OTHER PUBLICATIONS

Taylor, G. N., "X-Ray Resist Materials", *Solid State Technology*, May 1980, pp. 73–80.
Pastor, A. C. et al., "Lithography . . . Photoresists", *Thin Solid Films*, vol. 67, 1980, pp. 9–12.
Kuwano, H., et al., "Dry Development . . . Gallium Ion Beam", *Japanese Journal of Applied Physics*, vol. 19, #10, 10/80, pp. L615–L617.
Taylor, G. N., et al., "Oxygen Plasma . . . Polymer Films", Polymer Eng. & Science, 1980, vol. 20, No. 16, pp. 1087–1092.
Taylor, G. N., "X-Ray Resist Trends", Solid State Technology, pp. 124–131, 6/1984.

*Primary Examiner*—Charles L. Bowers, Jr.
*Attorney, Agent, or Firm*—James H. Fox

[57] ABSTRACT

Solid state devices are produced by dry etching of a resist film to produce a negative resist pattern. The film comprises a polymer typically containing a halogen, and at least one type of silicon-containing or nonsilicon-containing organometallic monomer. The radiation, typically X-ray radiation, locks the monomer or monomers into the polymer, with a subsequent fixing step removing the unlocked monomer or monomers in the unirradiated portion of the resist. The film is then exposed to a plasma comprising oxygen, which removes the unirradiated portion at a faster rate than the radiated portion, producing a negative resist pattern. The plasma development is typically accomplished by reactive ion etching. Sensitizers can be used to extend the wavelength response of the films, typically into the ultraviolet or visible regions.

11 Claims, No Drawings

PROCESS OF MAKING SOLID STATE DEVICES USING SILICON CONTAINING ORGANOMETALLIC PLASMA DEVELOPED RESISTS

This is a division of application Ser. No. 256,604, filed Apr. 22, 1981, U.S. Pat. No. 4,396,704.

BACKGROUND OF THE INVENTION

1. Field of the Invention

This invention relates to materials and methods for producing a negative tone resist pattern on a substrate when irradiated by actinic radiation and developed in a plasma atmosphere.

2. Description of the Prior Art

A process of dry etching to form negative resist patterns is described in U.S. Pat. No. 4,232,110, assigned to the same assignee as the present invention. In that technique, a film comprising a host polymer and one or more monomers is selectively irradiated to reduce the mobility of the monomer or monomers in the irradiated region, referred to as "locking". The film is then fixed, typically by means of heating, with or without a vacuum, to substantially remove the unlocked monomer mainly from the unirradiated region. It is then etched by means of a plasma, typically comprising oxygen. The locked monomer reduces the rate of etching in the irradiated region so that when the unirradiated region is etched down to the substrate, a negative resist pattern is formed. It is also disclosed therein that monomers containing silicon tend to yield negative resist patterns having a greater final thickness for a given initial thickness, as compared to typical nonsilicon-containing monomers.

It is also noted therein that bromine-containing host polymers are typically suitable for use with rhodium and certain other types of X-ray radiation sources. However, no silicon-containing monomer is therein disclosed that can be sufficiently locked into the brominated host polymer disclosed therein to yield a useful resist pattern. It is desirable to find other resist materials, including ones that yield improved sensitivity of the resist film. It is additionally desirable to find monomers that can be locked to a significant degree in a host polymer containing bromine.

SUMMARY OF THE INVENTION

I have invented resist film materials comprising at least one type of organometallic monomer and a host polymer. The organometallic monomers include both silicon-containing and nonsilicon-containing types. One or more types of monomer are locked in the host polymer by actinic radiation, and are subsequently fixed to reduce the amount of unlocked monomer in the unirradiated region of the resist film. The resist film is then developed by exposure to a plasma comprising oxygen. The oragnometallic monomers form a nonvolatile oxide during the oxygen plasma exposure. The silicon-containing organometallic monomers comprise members of the class of acrylates, or methacrylates, or vinylcarbazoles, or acenaphthalenes, or disiloxanes, or acrylamides. Typical nonsilicon organometallic monomers contain iron, germanium, or tin. Halogen-containing host polymers are typically suitable for irradiation by X-ray radiation. The use of a sensitizer allows other wavelength radiation, typically ultraviolet or visible radiation, to be utilized. Certain of the monomers are new compositions of matter with techniques for their preparation being shown.

DETAILED DESCRIPTION

The following detailed description relates to a procedure for making solid state devices by the use of improved resist materials comprising organometallic silicon-containing or nonsilicon-containing monomers.

The inventive resists can be used to form a pattern directly on a wafer, or an intermediate layer of a precursor device. They are useful for making semiconductor devices, including integrated circuits, or other solid state devices, including magnetic bubble devices, lightwave devices, etc. Alternately, the resists can be used to form a shadow mask that is separate from the device being produced. In addition, the inventive process and materials can be used to form patterns on printing plates, printed circuit boards, etc., or for information storage on laser-read discs, etc. The terms "solid state device" and "substrate", as used herein, include all such devices and layers, respectively.

In evaluating the inventive resists, the following terminology is used: the normalized thickness of the relief image after fixing is designated $NT_R$, and is the difference in thickness of the irradiated and unirradiated regions after fixing, divided by the initial thickness of the resist, which is typically about 1 micron for the Examples herein. The value of $NT_R$ gives a rough indication of how much of a given monomer is locked in the host polymer by the irradiation process. The normalized thickness of the relief image after plasma etching is designated $NT_D$, and is the difference in thickness of the irradiated and unirradiated regions after plasma etching, divided by the initial thickness of the resist. Since, for the Examples herein, the plasma etches the unirradiated region down to the substrate (0 thickness), $NT_D$ is simply the thickness of the irradiated region after etching divided by the initial thickness of the resist. In addition, the "differential etch ratio", as used herein, means the ratio of the thicknesses of material removed in a given amount of time by plasma etching in the unirradiated versus the irradiated regions of the resist. It is desirable to obtain a high value of $NT_D$, and this is typically achieved by obtaining a high differential etch ratio.

As noted in the above-referenced patent, halogen-containing polymers are typically utilized as the host polymer material when it is desired to use X-ray irradiation for forming the patterned image on the resist. The relative absorption characteristics of halogen-containing polymers are generally known in the art. For example, chlorine-containing polymers typically respond to X-ray radiation having a wavelength from about 2 to 4.5 Angstroms (0.2 to 0.45 nanometers), and from about 6 to 50 Angstroms (0.6–5.0 nanometers), whereas bromine-containing polymers typically respond to radiation in the 2 to 50 Angstrom (0.2 to 5 nanometer) range. Fluorine-containing polymers typically respond to wavelengths of 5 Angstroms (0.5 nanometers) or more. Copolymers or terpolymers comprising one or more halogen species are also possible host materials and may be designed to have broad wavelength sensitivity over a wide range of X-ray wavelengths. As used herein, the term "polymer" also includes copolymers and terpolymers. One host polymer comprising chlorine that is suitable for use with X-ray radiation is poly(2,3-dichloro-1-propyl acrylate), referred to herein as DCPA. A host polymer comprising bromine suitable for use with X-ray radiation is poly(2,3-dribromo-1-propyl acrylate), referred to herein as DBPA. The synthesis of these two host polymers is described in U.S. Pat. No. 4,061,829, assigned to the same assignee as the present invention.

A substrate coated with a film comprising the host polymer and one or more monomer types is irradiated by actinic radiation. The monomer should be efficiently locked in place by the radiation. In the dase of monomers locked by polymerization, this means that the ratio of the rate constant for the propagation step in polymerization during irradiation to the rate constant for chain termination ($K_p/K_t$) should be high, typically at least $10^5$ and preferably at least $10^6$. It has been found that five classes of silicon-containing monomers are locked with relatively high efficiency, and resulting high differential etch ratios and $NT_D$ values, in addition to the silicon-containing monomers noted in the above patent. These classes are acrylates, methacrylates, vinylcarbazoles, acenaphthalenes, and disiloxanes.

In addition, it has been found that metal-containing monomers can obtain a high $NT_D$ value. This is due to the formation of a metal oxide in the irradiated portion of the resist in the oxygen plasma atmosphere. If the metal oxide is nonvolatile under the processing conditions employed in the present technique, a protective oxide is left in the irradiated portion of the film wherein the metal-containing monomer is locked. This protective coating reduces the etch rate of the host polymer in the protected (irradiated) region, as compared to the unprotected (unirradiated) region. A similar oxide protection process is believed to occur for the silicon-containing monomers. A number of metals will form suitable protective oxides. Ideally, the metal-containing monomer should also be nontoxic, readily prepared, stable, and inexpensive. Three metallic elements stand out (in addition to silicon); Fe, Ge, and Sn. All can be covalently or coordinately bound in a variety of organic molecules.

As used herein, the term "organometallic" monomer means a monomer containing a metal bonded to carbon. Silicon, germanium, and other semiconductor or semimetallic species are considered to be metals for this purpose, as is consistent with current chemical terminology relating to organometallic compounds. For the purposes of the present invention, the organometallic monomers are thus divided into two classes: silicon-containing and nonsilicon-containing.

The monomer is typically of moderate volatility. Too high a volatility results in an unusably low shelf life for the monomer-polymer host material coated on a substrate prior to irradiation, whereas too low a volatility reduces the ease with which the monomer material is removed from the host polymer during the fixing process, which typically results in a reduced value of $NT_D$. The ease of monomer removal is also affected by the characteristics of the host polymer. For a rubbery host polymer, the molecular weight of the monomer typically should exceed 200 grams/mole but should be no greater than about 800 grams/mole to fulfill the foregoing conditions. For a glassy host polymer, the molecular weight of the monomer can be less to obtain a given degree of volatility, as compared to the monomer in a rubbery host polymer. Also, a polar monomer typically has a reduced volatility in a host polymer as compared to a nonpolar monomer of comparable molecular weight.

The etching of the resist after irradiation and fixing is accomplished by means of a plasma comprising oxygen. Other components may be included, including halocarbons as discussed below. For maximum etch uniformity across the surface of a wafer, it has been found desirable to use a reactive ion etching apparatus wherein an electrical bias is applied to the substrate to accelerate ions across a dark space. As used herein, the term "plasma" means an atmosphere having at least one ionized species, whether or not an acceleration is imparted to the species by an electrical bias.

To adequately cover nonplanar surface features, the present resists are advantageously used in conjunction with a planarizing layer. Methods of producing a planar layer include the so-called bilevel and trilevel processes, as they are known in the art. The trilevel process is described in U.S. Pat. No. 4,244,799, assigned to the same assignee as the present invention.

The above-noted principles will be more fully illustrated by means of the following Examples. In each of the Examples, the X-ray irradiation was conducted under a dry nitrogen atmosphere. The radiation chamber was flushed with dry nitrogen prior to introducing the sample therein, in order to prevent oxygen contamination that would reduce the sensitivity of the resist. The radiation was produced by electron bombardment of a Pd target to produce $Pd_{L\alpha}$ X-radiation at a wavelength of 4.37 Angstroms, at a dose rate of 2.9 $mj/cm^2$/minutes. The "fixing" step in each Example was accomplished by heating the irradiated film to 70 degrees Celsius under a vacuum of 0.5 torr for approximately 1 hour. Development was conducted, unless otherwise noted, either (1) at 0.5 torr pressure and 100 w power in a Dionex, Inc. Model 2005T-1813 SCA plasma etcher, or (2) at 0.025 torr pressure and 100 w power level by reactive ion etching (RIE). The substrate temperature during development was approximately 25 degrees Celsius.

EXAMPLE 1

The monomer used in this Example is p-trimethylsilylphenyl acrylate. It was prepared in four steps as follows:

(1) p-bromophenoxytrimethylsilane-86.5 g (0.50 mole) p-bromophenol was heated to 50 degrees Celsius. To it was added 44.8 g (0.28 mole) hexamethyldisilazane continuously over a period of 1 hour to prevent vigorous gas evolution. The temperature was maintained between 45 and 50 degrees Celsius for 2 hours. The resulting p-bromophenoxytrimethylsilane was vacuum distilled. 118.8 g of pure product was collected at 109.5 degrees Celsius and 14 mm Hg.

(2) p-trimethylsilylphenoxytrimethylsilane-5.35 g (0.22 mole) magnesium was added to 10 ml tetrahydrofuran and 0.35 ml $CH_3I$ under $N_2$ and heated to initiate the Grignard reaction. A solution of 49.0 g (0.2 mole) p-bromophenyoxytrimethylsilane and 63 ml tetrahydrofuran was added over a 1½ hour period. The reaction mixture was refluxed one additional hour and then cooled to room temperature. 22.8 g (0.21 mole) chlorotrimethylsilane was added to the reaction mixture. Once again the mixture was refluxed 1 hour and then cooled. 100 ml distilled water was slowly added, stirred, and separated. The organic phase was washed with two 50 ml portions of water and finally 50 ml of brine. The organic solution was dried over magnesium sulfate, filtered, and the solvent removed on a rotary evaporator under reduced pressure. Vacuum distillation gave 28.7 g of p-trimethylsilylphenoxytrimethylsilane, bp 132 degrees Celsius at 27 mm Hg.

(3) p-trimethylsilylphenol-28.7 g p-trimethylsilylphenoxytrimethylsilane was dissolved in 9 ml 95 percent ethyl alcohol. One drop of concentrated hydrochloric acid and 4 ml water were added, and the mixture was shaken for 5 minutes. After standing for another 15 minutes, the mixture was washed two times with 30 ml water and separated. The organic phase was poured into a crystallizing dish; p-trimethylsilylphenol crystallized out as white needles. After drying overnight in vacuo, 18.7 g of product was obtained (mp 76 degrees Celsius).

(4) p-trimethylsilylphenyl acrylate-8.32 g (0.05 mole) of p-trimethylsilylphenol was dissolved in 25 ml toluene. 6.1 g (0.06 mole) triethyl amine and 0.05 g hydroquinone was added. The solution was warmed. 5.43 g (0.06 mole) of acryloyl chloride was added over a 15 minute period. After 1½ hours, the solution was washed two times with 5 percent sodium carbonate in water and separated. After washing with brine and separating, the organic phase was dried over magnesium sulfate, filtered, and the solvent removed in a rotary evaporator under reduced pressure. Vacuum distillation yielded 9.2 g of pure p-trimethylsilylphenyl acrylate.

Pure p-trimethylsilylphenyl acrylate was mixed with chlorobenzene and poly(2,3-dichloro-1-propyl acrylate) to give a solution comprised of 17.5 parts acrylate, 24.8 parts DCPA, and 57.7 parts chlorobenzene. The solution was spin-coated at 2500 rpm on a Si wafer to give a 10200 Angstrom thickness coating. It was irradiated for 1 minute by $Pd_{L\alpha}$ X-radiation (2.9 mj/cm$^2$). Upon fixing, a relief image of 200 Angstroms was obtained, and the thickness remaining in the unirradiated regions was 6300 Angstroms; $NT_R=0.02$. Development by $O_2$ plasma etching for 3.6 minutes at 100 w gave a final thickness of 1500 Angstroms; $NT_D=0.15$. The differential removal rate was 361 Angstroms/minute, and the differential etch ratio was 1.26. The remaining resist layer was highly cracked. Nevertheless, 1 μm lines and spaces were resolved.

Increasing the radiation dose have the amount noted above yielded little increase in $NT_D$. This monomer has somewhat high volatility in the above polymer, in that approximately 15 percent of the monomer is lost upon setting for 1 hour after spin-coating. It is likely that replacement of a methyl group by a phenyl group will reduce this volatility. In addition, rather than using a rubbery host polymer such as DCPA, the use of a glassy polymer will tend to reduce the volatility of the monomer, allowing an increase in the time between resist coating and X-ray irradiation. The similar monomer p-trimethylsilylphenyl methacrylate is expected to give approximately equivalent results. In general, the percentages of these monomers in the DCPA host polymer may typically range from about 5 to 40 percent for usable results.

EXAMPLE 2

The monomer used in this Example is m-dimethylphenylsilylphenyl acrylate, which was prepared in four steps as follows:

(1) m-dimethylphenylsilylphenoxytrimethylsilane-5.35 g (0.22 mole) magnesium in a 500 ml three-necked flask was flame dried under nitrogen. 30 ml of tetrahydrofuran and 0.3 methyl iodide were added and gently heated to activate the magnesium. A solution of 45.8 g (0.20 mole) m-bromophenoxytrimethylsilane (prepared from m-bromophenol and hexamethyldisilazane in analogy to the preparation of the p-derivative in step 1 of Example 1) in 60 ml of tetrahydrofuran was added over 1 hour. To the heterogenous mixture was added 37.2 g (0.20 mole) chlorodimethylphenylsilane in 40 ml tetrahydrofuran. The reaction mixture was stirred overnight at room temperature. After cooling to 0 degrees Celsius, 100 ml water was slowly added. The organic layer was separated and subjected to two additional water washes and one final wash with brine. After drying over sodium sulfate and filtering, the solvent was removed under reduced pressure to give crude product.

(2) m-dimethylphenylsilylphenol-The fractions which contained high percentages of m-dimethylphenylsilylphenoxytrimethylsilane (as evidenced by GLPC and NMR) were dissolved in 10 ml ethyl alcohol. After addition of 1 drop concentrated HCl and 5 ml of water, the contents were shaken in a separatory funnel for 5 minutes and then allowed to separate. Washing with water was repeated. The organic phase was vacuum distilled to give 10.3 g of a mixture of m-dimethylphenylsilylphenol and other impurities collected at 127-145 degrees Celsius and 0.05 mm Hg as a colorless liquid.

(3) m-dimethylphenylsilylphenyl acrylate-10.3 g of of m-dimethylphenylsilylphenol was dissolved in 75 ml toluene. The mixture was cooled to 0 degrees Celsius in an ice bath. To it was added 8.1 ml (58 mmoles) of triethylamine. 3.3 ml (41 mmoles) of acryloyl chloride was added dropwise over a 15 minute period. After stirring overnight, the reaction mixture was cooled to 0 degrees Celsius. 25 ml of water was added slowly with stirring. The organic phase was then separated. The water wash was repeated and followed by washing with 25 ml of a saturated sodium chloride solution. The organic phase was dried over magnesium sulfate, filtered, and the solvents removed under reduced pressure. Attempts to purify the crude acrylate yielded fractions contaminated with the phenol. m-dimethylphenylsilylphenyl acrylate containing trace amounts of the corresponding phenol was obtained by passage through a bed of basic alumina.

A solution comprised of 89.1 parts chlorobenzene, 9.9 parts DCPA, and 0.99 parts m-dimethylphenylsilylphenyl acrylate was spin-coated on a Si wafer at 1900 rpm to give a 10300 Angstrom thick coating. Irradiation for 30 seconds (1.5 mj/cm$^2$) by $Pd_{L\alpha}$ X-rays, and subsequent fixing afforded a 100 Angstrom relief image and a thickness of 8700 Angstroms in the unirradiated regions; $NT_R=0.01$. $O_2$ plasma development as above for 4.4 minutes gave 2800 Angstroms of resist; $NT_D=0.27$. The differential etch ratio was 1.45. It was cracked but had submicrometer resolution in uncracked regions. A similarly exposed and fixed sample was developed by $O_2$ reactive ion etching at 0.03 torr and 100 w for 6.5 minutes to give 1200 Angstrom resist ($NT_D=0.12$) with no cracking and submicrometer resolution.

EXAMPLE 3

This Example shows the use of the same monomer as in Example 2 in a host polymer that is a chloro-bromo copolymer.

A solution comprising 85.5 parts chlorobenzene, 13.1 parts of a 50:50 mole percent copolymer of 2,3-dibromo-1-propyl acrylate and 2,3-dichloro-1-propyl acrylate, and 1.4 parts m-dimethylphenylsilylphenyl acrylate was coated on a Si wafer by spinning at 3000 rpm. This gave a resist thickness of 10100 Angstroms. Irradiation for 30 seconds by $Pd_{L\alpha}$ radiation and fixing gave a 200 Angstrom relief image and an unirradiated region thickness of 8700 Angstroms; $NT_R=0.02$. Development by $O_2$ reactive ion etching for 5.6 minutes gave a final thickness of 1800 Angstroms ($NT_D=0.18$), submicrometer resolution, and no cracking. The differential etch ratio was 1.23.

EXAMPLE 4

This Example shows the use of the same monomer as in Examples 2 and 3, but with a bromine-containing host polymer.

A solution containing 89 parts chlorobenzene, 9.9 parts poly(2,3-dibromo-1-propyl acrylate), and 1.1 parts m-dimethylphenylsilylphenyl acrylate was spin-coated onto a Si wafer at 1000 rpm to give a 6800 Angstrom thick coating. The material was irradiated for 30 seconds by $Pd_{L\alpha}$ X-rays (1.5 mj/cm$^2$) and fixed as above to give a 300 Angstrom relief image and 4600 Angstrom thickness in the unirradiated regions; $NT_R=0.04$. Development for 6 minutes by $O_2$ reactive ion etching gave 2100 Angstrom thick patterns ($NT_D=0.31$) with submicrometer resolution and no cracking. The differential etch ratio was 1.64.

EXAMPLE 5

Another class of acrylic silanes which is useful includes the aliphatic bis-acryloxy- and methacryloxyalkyltetramethyldisiloxanes of general structure (1).

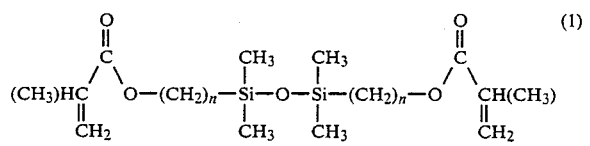

The number of methylene groups n can be varied, thus affording a variety of materials providing a broad range of molecular weights and volatilities. Metal content is high for low values of n, which is desirable for maximum etch resistance to the oxygen plasma. The butyl (n=4) analogues are very useful. Acrylate and methacrylate esters have been prepared from the corresponding diol in good yields. The acrylate has also been prepared directly from the cyclic siloxane (1,1-dimethyl-1-sila-2-oxacyclohexane) by acid catalyzed reaction with acryloyl chloride, as follows: In a flask was placed 13 g (0.1 moles) of the cyclic siloxane, 9.5 g (0.11 moles) acryloyl chloride, 85 ml benzene, 0.3 g aluminum trichloride, and 0.1 g hydroquinone. The mixture was stirred and heated at reflux for 10 hours. Upon cooling, 6 ml of water was added, and the sample was shaken. The aqueous layer was drawn off, and the benzene was removed under vacuum on a rotary evaporator. The residue was distilled to give 7.1 g of bis-acryloxybutyl-tetramethyldisiloxane (BABTDS) with bp 153-155 degrees Celsius at 0.1 torr pressure.

Both the acrylate and methacrylate esters have appropriate volatility and are compatible with DCPA at low concentrations. The methacrylate is less soluble and is incompatible with DCPA at $\geq 10$ weight percent monomer. Both materials are very sensitive. For each, the optimum concentration of monomer affords a normalized thickness of 0.40 for a 1 minute irradiation time. An even higher sensitivity is obtained when BABTDS is purified after the above-noted preparation steps. The values of $NT_R$ and $NT_D$ for BABTDS as a function of irradiation time are shown in Table 1, along with the differential removal rate $R_D$. $R_D$ is defined as the difference in the removal rates in the oxygen plasma for the unirradiated and irradiated regions. At higher doses (4 minute irradiation), essentially complete retention of the initial spun thickness is attained for the acrylate.

TABLE 1
Properties Of 90:10 DCPA-BABTDS As A Function Of Irradiation Time

| X-Ray Irradiation Time (Min.) | $NT_R$ | $NT_D$ | $RD_D$ (Å/Min.) |
|---|---|---|---|
| 0.5 | 0.02 | 0.15 | 216 |
| 1.0 | 0.05 | 0.43 | 633 |
| 2.0 | 0.07 | 0.77 | 1166 |
| 4.0 | 0.08 | 0.97 | 1433 |

Thus, bis-acryloxybutyltetramethyldisiloxane in DCPA host is a very sensitive plasma-developed resist. However, in films having a final thickness >3000 Angstroms, ($NT_D>0.30$ for 1 micron initial thickness), it is highly cracked.

The cracking is believed to be due to fracturing of a continuous $SiO_2$ layer formed on top of the thicker organosilicon layer. The cracking can be eliminated typically in two ways: (1) introduction of a halocarbon, typically a fluorocarbon gas, into the oxygen during plasma etching; (2) use of oxygen reactive ion etching instead of plasma etching. In the former case, $SiO_2$ is presumably etched by the halocarbon, e.g., $CF_2$, produced in the plasma, whereas in reactive ion etching, some of the $SiO_2$ may be removed by physical sputtering.

In Tables 2 and 3 are data for the former case, plasma etching in freon gas-$O_2$ mixtures. Addition of small amounts of freon increases the removal rate due to the well-known effect of fluorine atom catalysis. For both $CF_4$ and $CF_3Cl$ gases, resist cracking is eliminated at high freon gas concentrations but at the expense of thickness (lower $NT_D$). Resolution likewise improves. Note that equivalent effects are achieved for $CF_3Cl$ at much lower concentrations (Table 3). This is probably because a $CF_3Cl$ plasma efficiently etches $SiO_2$, while a $CF_4$ plasma removes $SiO_2$ more slowly.

TABLE 2
Influences Of Added $CF_4$ On $O_2$ Plasma Etching Of 90:10 DCPA-BABTDS Irradiated For 4 Min.

| Conc. $CF_4$ In $O_2$ (ppm) | Etch Time (Min.) | $NT^D$ | Cracks? | Resol'n |
|---|---|---|---|---|
| 0 | 30 | 0.98 | Extensive | Poor |
| 134 | 19 | 0.65 | Yes | Poor |
| 1280 | 5.8 | 0.48 | Slight | Fair |
| 7840 | 4.0 | 0.37 | No | Fair |
| 9460 | 2.3 | 0.33 | No | Good (1 μm) |

TABLE 3
Influence Of Added $CF_3Cl$ On $O_2$ Plasma Etching Of 90:10 DCPA-BABTDS Irradiated For 4 Min.

| $CF_3Cl$ In $O_2$ (ppm) | Etch Time (Min.) | $NT^D$ | Cracks? | Resol'n |
|---|---|---|---|---|
| 0 | 30 | 0.98 | Extensive | Poor |
| 31 | 22 | 0.48 | Yes | Poor |
| 62 | 17 | 0.36 | Slight | Fair |
| 93 | 7.0 | 0.15 | No | Good |
| 233 | 7.0 | 0.07 | No | V. Good (<1 μm) |

Pattern development using refractive ion etching with $O_2$ at 25 mtorr pressure produces a crack-free, fully developed film independent of dose. This may result from sputter etching of $SiO_2$ formed on the surface during $O_2$ RIE removal. Pure $SiO_2$ sputters at approximately 30 Angstroms/minute under these conditions, whereas the irradiated and unirradiated resist regions etch at rates between 400 and 1800 Angstroms/minute, depending on composition and dose. RIE development results in lower $NT_D$ values (less selective) for all the irradiation doses. However, the sensitivity is still high enough to realize short irradiation times. For example, with a 1.5 μm initial film thickness, a 60 second exposure affords 0.37 μm final resist thickness. This is quite adequate for subsequent $SiO_2$ etching used in the above-noted trilevel process. The optimum composition for the lowest irradiation dose which provides 2500–3000 Angstrom final resist thickness appears to be the 90:10 DCPA-BABTDS mixture. The bis-methacryloxybutyltetramethyldisiloxane monomer also gives good results at concentrations <10 weight percent in DCPA.

EXAMPLE 6

In this Example, the silicon-containing monomer is 3-trimethylsilyl-9-vinylcarbazole. It was prepared in two steps as follows:

(1) 3-Bromo-9-vinylcarbazole-3-Bromocarbazole (24.6 g, 0.1 mole) was dissolved in acetone. To it was added β-chloroethyltoluenesulfonate (31.68 g, 0.135 moles) and sodium hydroxide (13 g, 0.325 mole) dissolved in 10 ml of distilled water. The mixture was brought to reflux. After 24 hours, equal amounts of β-chloroethyltoluenesulfonate, sodium hydroxide, and water were added. Refluxing was continued until 3-bromo-9-(2-chloroethyl)-carbazole was formed in >95 percent yield as judged by GLPC analysis. The product was dissolved in a mixture of 250 ml diethyl ether and tetrahydrofuran (50:50 v/v) and washed successively with two 150 ml portions of distilled water and 100 ml saturated sodium chloride solution. The organic phase was separated and dried over sodium sulfate and filtered. Solvents were removed on a rotary evaporator at reduced pressure. The crude 3-bromo-9-(2-chloroethyl)carbazole was dissolved in 230 ml isopropanol. 8.4 g (0.15 mole) potassium hydroxide dissolved in 15 ml ethanol was added. The resulting solution was refluxed for 1½ hours. 4.2 g of solid potassium hydroxide was then added, and refluxing was continued for an additional 1½ hours. The solution was cooled in a freezer during which time a solid residue formed. After filtration, the solid was washed with water. Recrystallization from methanol gave 13.94 g 3-bromo-9-vinylcarbazole as pale yellow-white needles (mp 74–74.5 degrees Celsius).

(2) 3-trimethylsilyl-9-vinylcarbazole—5.0 g (0.018 moles) of 3-bromo-9-vinylcarbazole was dissolved in 50 ml tetrahydrofuran under a nitrogen atmosphere. The solution was cooled to −78 degrees Celsius. 15.8 ml of 1.28M n-butyl lithium in hexane was added dropwise over a 15 minute period. The heterogeneous mixture was stirred an additional hour. 2.4 ml (0.019 mole) of chlorotrimethylsilane was added dropwise over a 10 minute span and was stirred 1 hour longer. The mixture was allowed to warm to room temperature. 30 ml of 5 percent solution of sodium bicarbonate in water was slowly added, stirred, and then separated. The organic phase was washed repeatedly with water and finally with saturated sodium chloride in water. After drying over sodium sulfate, the solution was filtered and the solvent removed on a rotary evaporator under reduced pressure to give 5.5 g of a pale yellow oil. The oil was chromatographed on basic alumina with a mixture of hexane and benzene as eluent to give 2.5 g of 95 percent pure 3-trimethylsilyl-9-vinylcarbazole obtained as a colorless oil.

A solution containing 87.8 parts chlorobenzene, 9.8 parts poly(2,3-dichloro-1-propyl acrylate), and 2.4 parts 3-trimethylsilyl-9-vinylcarbazole was spin-coated at 2100 rpm on a Si wafer to give a 10200 Angstrom coating. Upon irradiation by $Pd_{L\alpha}$ X-rays for 15 seconds (0.7 mj/cm$^2$) and fixing, a 200 Angstrom relief image was obtained; $NT_R=0.02$. The unirradiated regions had a residual thickness of 7800 Angstroms. Development by reactive ion etching gave 1200 Angstroms thickness; $NT_D=0.12$. The differential etch ratio was 1.15. Phase separation appeared to occur on features <2.0 μm.

EXAMPLE 7

This Example uses the same monomer as in Example 6, but with poly(2,3-dibromo-1-propyl acrylate) substituted for the DCPA. Thus, a mixture containing 9.8 parts DBPA, 87.8 parts chlorobenzene, and 2.4 parts 3-trimethylsilyl-9-vinylcarbazole was spin-coated at 600 rpm onto a Si wafer to give an 8500 Angstrom coating. Upon irradiation for 7.5 seconds (0.36 mj/cm$^2$) by $Pd_{L\alpha}$ X-rays and fixing, a 600 Angstrom relief image was obtained with 6600 Angstroms remaining in the unirradiated regions; $NT_R=0.07$. Reactive ion etching in $O_2$ for 5.25 minutes afforded a 2800 Angstrom mottled pattern with 2 μm resolution; $NT_D=0.33$. The differential etch ratio was 1.50. The resolution was also limited by phase separation. Improved resolution can be expected for improved host polymer/monomer compatibility.

EXAMPLE 8

In this Example, the silicon-containing monomer is 3-dimethylphenylsilyl-9-vinylcarbazole. It was prepared as follows: 8.16 g (30 mmoles) of 3-bromo-9-vinylcarbazole was placed in a flask. 100 ml of tetrahydrofuran was added to the flask. Upon dissolution of 3-bromo-9-vinylcarbazole, the solution was cooled to −78 degrees Celsius. 28.1 ml of sec-butyl lithium (1.12M in cyclohexane) was added dropwise over a 50 minute period. The resultant heterogeneous slurry was stirred an additional 20 minutes. 5.12 g (30 mmoles) of dimethylphenylchlorosilane dissolved in 10 ml of tetrahydrofuran was added to the reaction mixture dropwise over 7 minutes. The slurry was stirred for an additional 60 minutes and then allowed to warm to room temperature. The reactant solution was quenched by the slow addition of 50 ml of a 10 percent aqueous sodium bicarbonate solution. The organic layer was separated and washed successively with 50 ml of a 5 percent aqueous sodium hydroxide solution, 50 ml distilled water, and 50 ml of saturated sodium chloride solution. After drying over magnesium sulfate and filtering, the solvents were removed on the rotary evaporator to yield 9.38 g of crude material as a thick yellow oil. White insoluble material of unknown structure was removed after triturating with hexane and filtering the mixture. The resulting yellow oil contained 77 percent 3-dimethylphenylsilyl-9-vinylcarbazole. Major impurities were N-vinylcarbazole (19 percent) and small percentages of unidentified materials.

The mixture of carbazoles was evaluated as an X-ray resist using DCPA host. Thus, a solution comprised of 87.8 parts chlorobenzene, 2.4 parts crude 3-dimethylphenylsilyl-9-vinylcarbazole, and 9.8 parts DCPA was spin-coated onto a Si wafer at 2300 rpm, affording a 10000 Angstrom thick film. It was irradiated for 2.0 minutes (5.8 mj/cm²) by $Pd_{L\alpha}$ X-radiation and fixed as above to give 8300 Angstroms in the unirradiated regions and a relief image of 800 Angstroms; $NT_R=0.08$. Development by $O_2$ reactive ion etching for 12 minutes gave a crack-free 2800 Angstrom thick pattern with submicron resolution; $NT_D=0.28$. The differential etch ratio was 1.32. No defect sites attributable to phase separation were evident.

EXAMPLE 9

The monomer used in this Example is 5-dimethylphenylsilylacenaphthalene, prepared as follows:

(1) 5-dimethylphenylsilylacenaphthene-11.66 g (50 mmoles) of 5-bromoacenaphthene was dissolved in 100 ml tetrahydrofuran under a nitrogen atmosphere. The solution was cooled to −78 degrees Celsius at which time 52 ml of 1.05M sec-butyl lithium in cyclohexane was added over a 1 hour period. 9.39 g (55 mmoles) of dimethylphenylchlorosilane dissolved in 15 ml of tetrahydrofuran was slowly added dropwise. After stirring for an additional ½ hour at −78 degrees Celsius, the solution was allowed to warm to room temperature. 50 ml of 10 weight percent aqueous ammonium chloride was slowly added and the mixture shaken and separated. The organic phase was successively washed with 50 ml of 10 percent ammonium chloride, 50 ml of distilled water, and 50 ml saturated sodium chloride. The organic layer was dried over sodium sulfate and filtered. The solvent phase was removed on a rotary evaporator under reduced pressure to yield 10.6 g of crude 5-dimethylphenylsilylacenaphthene. Purity was 95 percent, as determined by GLPC. The resultant oil crystallized upon standing (mp 48–58 degrees Celsius).

(2) 5-dimethylphenylsilylacenaphthylene-10.2 g (32.4 mmoles) of the crude 5-dimethylphenylsilylacenaphthene was dissolved in 140 ml tetrahydrofuran. After cooling to −78 degrees Celsius, 55 ml of 1.44M sec-butyl lithium in cyclohexane was added over a 1 hour period. The resultant dark reddish violet solution was stirred an additional ½ hour to effect dilithiation. 9.89 g (78 mmoles) of iodine dissolved in 40 ml tetrahydrofuran was added over 10 minutes. After stirring ½ hour at −78 degrees Celsius, the solution was warmed to room temperature. 100 ml of 10 percent sodium thiosulfate in water was slowly added and the organic phase separated. Work-up continued with one additional sodium thiosulfate wash. After the organic phase was washed with distilled water and saturated sodium chloride, it was dried over sodium sulfate and filtered. The solvent was removed on a rotary evaporator to give a residue. Crystallization of it from ethyl ether gave 6.10 g of 5-dimethylphenylsilylacenaphthylene as orange-yellow plates (mp 63–64 degrees Celsius).

A 10000 Angstrom thick coating on a Si wafer was obtained by spin-coating a solution containing 87.8 parts chlorobenzene, 9.8 parts DCPA, and 2.4 parts 5-dimethylphenylsilylacenaphthalene at 2400 rpm. The sample was irradiated for 2.0 minutes (5.8 mj/cm²) by $Pd_{L\alpha}$ X-radiation. Fixing by heating in a vacuum gave a relief image thickness of 800 Angstroms and a thickness in the unirradiated regions of 8600 Angstroms; $NT_R=0.08$. Treatment for 6¼ minutes by $O_2$ reactive ion etching afforded a developed thickness of 1800 Angstroms with submicron resolution; $NT_D=0.18$. The differential etch ratio was 1.13. Film quality was excellent with no evidence of phase separation or cracking.

EXAMPLE 10

This Example shows the use of a nonsilicon-containing organometallic monomer.

A solution containing 9.9 parts poly(2,3-dichloro-1-propyl acrylate), 89 parts chlorobenzene, and 1.1 parts diphenyldivinyltin was spin-coated at 1600 rpm onto a Si wafer to give a 10000 Angstrom film. It was irradiated by $Pd_{L\alpha}$ X-rays for 1 minute (2.9 mj/cm²) and fixed to give a 100 Angstrom relief image and 8500 Angstrom residue in the unirradiated areas; $NT_R=0.01$. Development by $O_2$ plasma etching afforded submicrometer resolution patterns 1900 Angstroms thick; $NT_D=0.19$. The differential etch ratio was 1.27. No evidence of cracking was present. Irradiation for more than 2 minutes resulted in ≧3500 Angstrom thick patterns which were highly cracked.

The above results and general knowledge of the art show that useful classes of silicon monomers to be (1) dimethylphenylsilyl substituted aromatic acrylates, methacrylates, vinylcarbazoles, and acenaphthalenes; (2) trimethylsilyl substituted aromatic acrylates, methacrylates, vinylcarbazoles, and acenaphthalenes; and (3) bis-acryloxy- or methacryloxyalkyltetramethyldisiloxanes.

Other Monomers and Polymers

Based upon the experience with the above-noted silicon-containing monomers, it is apparent that still other types of monomers, including the aromatic acrylamide class, are suitable for practicing the present invention. These monomers are typically of the following representative forms and isomers thereof:

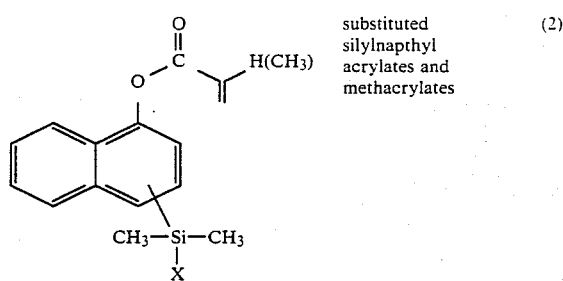

substituted silylnapthyl acrylates and methacrylates (2)

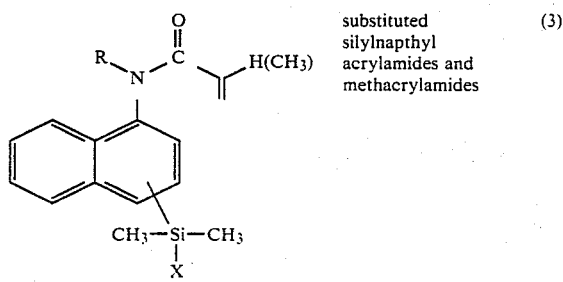

substituted silylnapthyl acrylamides and methacrylamides (3)

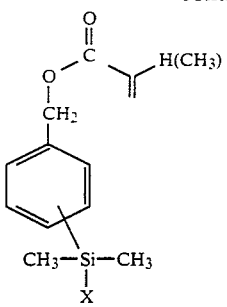
(4) substituted silylbenzyl acrylates and methacrylates

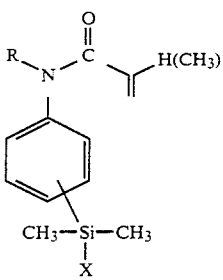
(5) substituted silylphenyl acrylamides and methacrylamides where: X = CH₃, C₆H₅, (CH₂)₃CN, C₂H₅, and R = H, CH₃, or

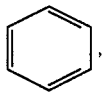

both chosen for proper volatility and compatability with the host polymer.

In addition, host polymers of the following types are expected to be useful, where Z is F, Cl, Br, or I:

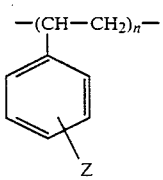
(6) halogen substituted poly(styrenes)

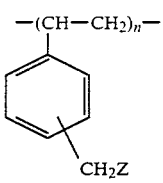
(7) halomethyl poly(styrenes)

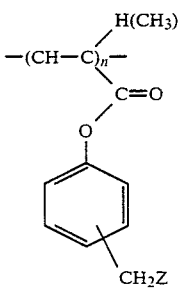
(8) halomethyl substituted poly(phenyl acrylates) and methacrylates

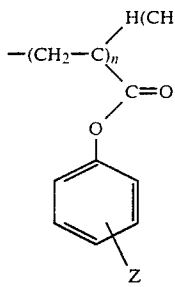
(9) halogen substituted poly(phenyl acrylates) and methacrylates

In addition to X-ray radiation of various wavelengths, the present inventive materials can be used with other types of radiation, including ultraviolet and visible light, typically with the use of a sensitizer in the film. For example, the films of Examples 2–5 can be made more sensitive to UV radiation in the range of about 280 to 330 nanometers by including about 1 to 10 weight percent of 1,1-dimethoxy-1-phenylacetophenone in the films. The film of Example 6 can be sensitized to UV radiation in that range by including about 1 to 5 weight percent of phenanthroquinone in the film. Other sensitizers can be used for other wavelength radiation, according to principles known in the resist art. The halogen-containing host polymers are especially useful for X-ray radiation and ultraviolet radiation. However, nonhalogen-containing polymers may be used, typically for other wavelength radiation. The absorption characteristics of the polymer should be matched to the radiation used, according to principles known in the resist art. In some cases, the choice of appropriate polymers may make the use of a sensitizer unnecessary for UV or visible radiation.

While the present invention concerns organometallic monomers (both silicon and nonsilicon), nonorganometallic (i.e., organic) monomers that are locked in the host polymer can also be included in the film. For example, the above-noted U.S. Pat. No. 4,232,110 discloses that the presence of two monomer types increases the differential etch ratio in some cases. Furthermore, the presence of an organic monomer in some cases allows the incorporation of organometallic monomers that would otherwise be relatively incompatible with the host polymer.

All such variations and deviations which basically rely on the teachings through which this invention has advanced the art are properly considered to be within the spirit and scope of the invention.

What is claimed is:

1. In a method of producing a solid state device that includes at least one pattern delineation steps, the steps comprising:
   (a) selectively irradiating a resist film on a substrate with actinic radiation, wherein said film comprises a polymer and at least one type of monomer;
   (b) treating said film to reduce the amount of said at least one type of monomer in the unirradiated portion of said film; and
   (c) developing said film in a plasma comprising oxygen, thereby removing the unirradiated portion of the film at a faster rate than the irradiated portion, thereby producing a negative resist pattern, the invention CHARACTERIZED in that said at least one type of monomer includes at least one type of silicon-containing organometallic monomer selected from the group consisting of bis-acryloxybutyltetramethyldisiloxane, bis-methacryloxybutyltetramethyldisiloxane, m-dimethylphenylsilylphenyl acrylate or methacrylate.

2. The method of claim 14 FURTHER CHARACTERIZED in that said at least one type of silicon-containing organometallic monomer is m-dimethylphenylsilylphenyl acrylate, and said polymer is poly(2,3-dichloro-1-propyl acrylate) or poly(2,3-dibromo-1-propyl acrylate) or a copolymer thereof.

3. The method of claim 1 FURTHER CHARACTERIZED in that said at least one type of silicon-containing organometallic monomer is bis-acryloxybutyltetramethyldisiloxane, and said polymer is poly(2,3-dichloro-1-propyl acrylate).

4. The method of claim 1 FURTHER CHARACTERIZED in that said plasma further comprises at least one halocarbon species so that cracking of said film is substantially eliminated.

5. The method of claim 1 FURTHER CHARACTERIZED in that an electrical bias is applied to said substrate relative to the source of said plasma, whereby said developing is accomplished by reactive ion etching.

6. The method of claim 1 FURTHER CHARACTERIZED in that said polymer is poly(2,3-dichloro-1-propyl acrylate), or poly(2,3-dibromo-1-propyl acrylate), or a copolymer thereof.

7. The method of claim 1 FURTHER CHARACTERIZED in that said resist film further comprises a sensitizer to enhance the sensitivity of said resist to ultraviolet or visible radiation.

8. The method of claim 1 FURTHER CHARACTERIZED in that said polymer is a rubbery polymer, and said film comprises at least one silicon-containing organometallic monomer type having a molecular weight in the range of 200 grams/mole to 800 grams/mole.

9. The method of claim 1 FURTHER CHARACTERIZED in that said polymer is a glassy polymer.

10. The method of claim 1 FURTHER CHARACTERIZED in that one type of monomer is m-dimethylphenylsilylphenyl acrylate.

11. The method of claim 1 FURTHER CHARACTERIZED in that one type of monomer is bis-acryloxybutyltetramethyldisiloxane.

* * * * *

UNITED STATES PATENT AND TRADEMARK OFFICE
CERTIFICATE OF CORRECTION

PATENT NO. : 4,500,628

DATED : February 19, 1985

INVENTOR(S) : Gary N. Taylor

It is certified that error appears in the above-identified patent and that said Letters Patent is hereby corrected as shown below:

Column 3, line 8, "dase" should read --case--. Column 8, line 48, "$NT^D$" should read --$NT_D$--; line 60, "$NT^D$" should read --$NT_D$--; line 66, "refractive" should read --reactive--. Column 11, line 66, "6 1/3" should read --6 2/3--. Column 15, line 6, "14" should read --1--.

*Signed and Sealed this*

Sixteenth *Day of* July 1985

[SEAL]

*Attest:*

DONALD J. QUIGG

*Attesting Officer*  *Acting Commissioner of Patents and Trademarks*